United States Patent
Chen et al.

(10) Patent No.: US 7,760,852 B2
(45) Date of Patent: Jul. 20, 2010

(54) X-CT SCAN SYSTEM

(75) Inventors: Zhiqiang Chen, Beijing (CN); Kejun Kang, Beijing (CN); Li Zhang, Beijing (CN); Haifeng Hu, Beijing (CN); Yuxiang Xing, Beijing (CN); Liang Li, Beijing (CN); Yongshun Xiao, Beijing (CN); Ziran Zhao, Beijing (CN); Yuanjing Li, Beijing (CN); Yinong Liu, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 12/159,640

(22) PCT Filed: Dec. 14, 2006

(86) PCT No.: PCT/CN2006/003417

§ 371 (c)(1),
(2), (4) Date: Jul. 8, 2008

(87) PCT Pub. No.: WO2007/076681

PCT Pub. Date: Jul. 12, 2007

(65) Prior Publication Data

US 2009/0003516 A1    Jan. 1, 2009

(30) Foreign Application Priority Data

Dec. 31, 2005    (CN)    .................. 2005 1 0135935

(51) Int. Cl.
  *A61B 6/00*  (2006.01)
(52) U.S. Cl. .......................................... 378/19; 378/20
(58) Field of Classification Search .................. 378/4, 378/19, 20, 27, 62, 195, 208
See application file for complete search history.

(56) References Cited

U.S. PATENT DOCUMENTS

| | | | | |
|---|---|---|---|---|
| 4,600,998 A | * | 7/1986 | Huet | 702/40 |
| 5,119,408 A | * | 6/1992 | Little et al. | 378/4 |
| 6,359,955 B1 | | 3/2002 | Nukui | 378/4 |
| 2004/0013225 A1 | | 1/2004 | Gregerson et al. | 378/19 |
| 2009/0074136 A1 | * | 3/2009 | Kamegawa | 378/20 |

* cited by examiner

FOREIGN PATENT DOCUMENTS

CN    1271261    10/2000

OTHER PUBLICATIONS

"International Search Report and Written Opinion" for related Application No. PCT/CN2006/003417, 7 pages, (Sep. 3, 2007).

*Primary Examiner*—Irakli Kiknadze
(74) *Attorney, Agent, or Firm*—Westman, Champlin & Kelly, P.A.

(57) ABSTRACT

An X-CT scan system includes a base, an object rotary support, an X-ray generation device and a data acquisition system, wherein one side of the detector is leveled to or beyond the prolong line of the connecting line between the X-ray source of the X-ray generation device and the center of the object rotary support, the length of the beyond portion is less than the radius of the imaging field. The advantage of the invention is in that the invention can reconstruct the entire image of the object by means of X-ray projection data which only covers half of the area of the object. Compared with the traditional CT scan system, half of the detector size can be saved at most. The X-CT scan system is simplified and the projection data amount for scan and computation amount for image reconstruction are also reduced with the reconstructed image quality guaranteed.

3 Claims, 3 Drawing Sheets

FIG. 4(a)
FIG. 4(b)
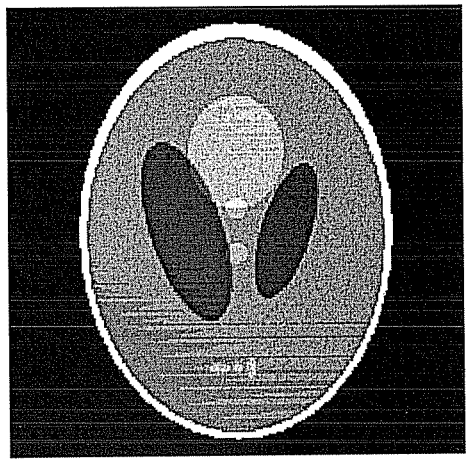 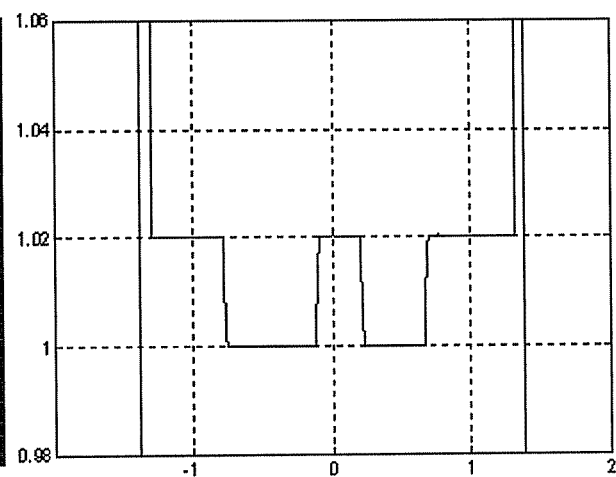
FIG. 5
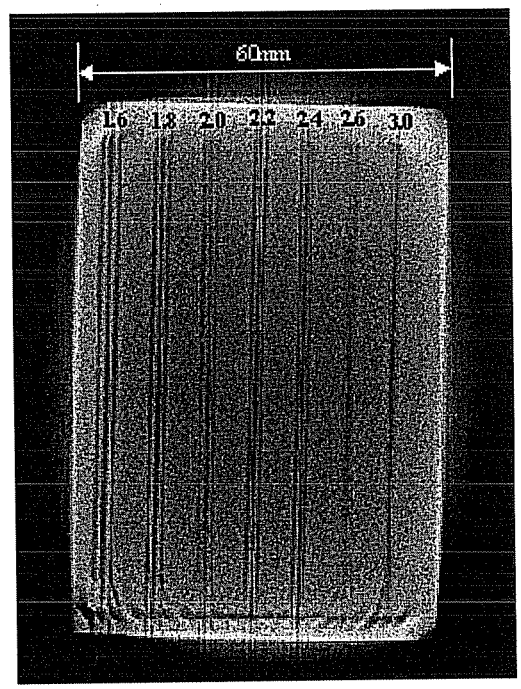

X-CT SCAN SYSTEM

CROSS-REFERENCE TO RELATED APPLICATION

This Application is a Section 371 National Stage Application of International Application No. PCT/CN2006/003417, filed Dec. 14, 2006, not yet published, the content of which is hereby incorporated by reference in its entirety.

FIELD OF THE INVENTION

The present invention relates to an X-CT scan system, and more particularly to an X-CT scan system with a detector positioned off-center.

BACKGROUND OF THE INVENTION

The computerized tomography (CT) technology has been widely used for the medical diagnosis and the industrial non-destructive inspection. In various CT systems, the mostly-used ones are fan-beam or cone-beam X-CT systems. The existing X-CT scan systems adopt a circular orbit scan mode and a linear array detector (corresponding to the fan-beam X-CT) or a planar array detector (corresponding to the cone-beam X-CT) because the circular orbit scan mode only requires a simple and easy implemented mechanical structure, and the corresponding reconstruction algorithm has been developed and is reliable. Furthermore, the detectors are placed symmetrically with respect to the connecting line from the X-ray source to the rotation axis or slightly deviated in the case of detector slightly-moving technique. Particularly, the circular orbit scan mode based X-CT system plays an important role in the industrial non-destructive inspection hitherto.

Among the circular orbit cone-beam or fan-beam CT reconstruction algorithms, the filtered-backprojection (FBP) algorithm is widely used, which has several advantages such as simple mathematical equation, quick computation, easy implementation and so on. The famous FDK algorithm, for example, is a FBP algorithm. However, the conventional FBP algorithm requires the projection data can not be truncated in the detector direction, which means that the detector must be long enough in the transverse direction to cover the entire cross section of the object. Therefore, when the object under measure has a large volume, the X-ray beams need to have a large spread angle and the detector needs to be large in size to completely cover the object. These requirements are hard to meet in some applications.

When a large cross section object is to be measured, one practical method is to use the second generation scan mode, rotation plus shift. In particularly, the entire object is covered through several scans firstly, and then the whole projection data is obtained by means of a rebinning method. However, the scan mode is long in time and costs much effort, which largely adds the hardware complexity and overhead of the system, and the data amount is doubled and the computation is also increased, thus the reconstruction speed is lowed.

According to the CT scan principle and the reconstruction theory, in the case of circular orbit scan, reconstructing mathematically the whole object does not need all the projection data which covers the whole object in 360 degrees. In principle, the projection data is redundant by half, that is to say, half of the projection data is redundant. Therefore, only half of the projection data is needed to accurately reconstruct the whole object tomographic images.

SUMMARY OF THE INVENTION

An object of the present invention is to overcome the above disadvantages in the prior art, and to provide a X-CT scan system which has a simple structure and a low cost, and can reduce the projection data amount for scan and computation amount for image reconstruction.

In an aspect of the invention, an X-CT scan system is provided, which comprises a base, an object rotary support placed in the base which is for placing the object under inspection, an X-ray generation device and a data acquisition system, which are at two sides of the base, wherein one side of the detector is leveled to or beyond the prolong line of the connecting line between the X-ray source of the X-ray generation device and the center of the object rotary support, the length of the beyond portion is less than the radius of the imaging field. Preferably, one side of the detector is leveled to the prolong line of the connecting line between the X-ray source of the X-ray generation device and the center of the rotary support, or beyond the latter by 1% of the radius of the imaging field.

Preferably, the detector is a linear array detector a curve array detector or, a planar array detector or a bend planar array detector.

Preferably, the X-ray generation device comprises an X-ray tube, an X-ray accelerator, or a radiation source.

Using the X-CT scan system according to the present invention, the detector and the X-ray source of the X-ray generation device are positioned off-center with respect to the center of the rotary support, which can solve the CT reconstruction problem of the cross section projection data, including the problem of the fan-beam CT and cone-beam CT. When the X-CT system according to the invention is used, the object to be inspected is place at the center of the rotary support. The entire object tomographic images can be reconstructed by means of the X-ray projection data which only covers half of the cross section of the object to be reconstructed. Compared with the conventional X-CT scan system, nearly half detector can be omitted, and thus the X-CT scan system is simplified and the projection data amount for scan and computation amount for image reconstruction are reduced on the premise that the image reconstruction quality is insured. Meanwhile, the hardware cost of the system can be largely decreased.

BRIEF DESCRIPTION OF THE DRAWINGS

The above advantages and features of the present invention will be apparent from the following detailed description on the preferred embodiments taken conjunction with the drawings in which:

FIG. 4(a) is an image reconstructed by means of fan-beam detector scan data in a Shepp-Logan head model simulation experiment;

FIG. 4(b) is a profile from the middle line of the image of FIG. 4(a);

FIG. 5 is a resulting image reconstructed by the experiment data made by means of a pair-line card on a 450 Kev cone-beam CT system.

REFERENCE NUMERAL LIST

Figure 1:
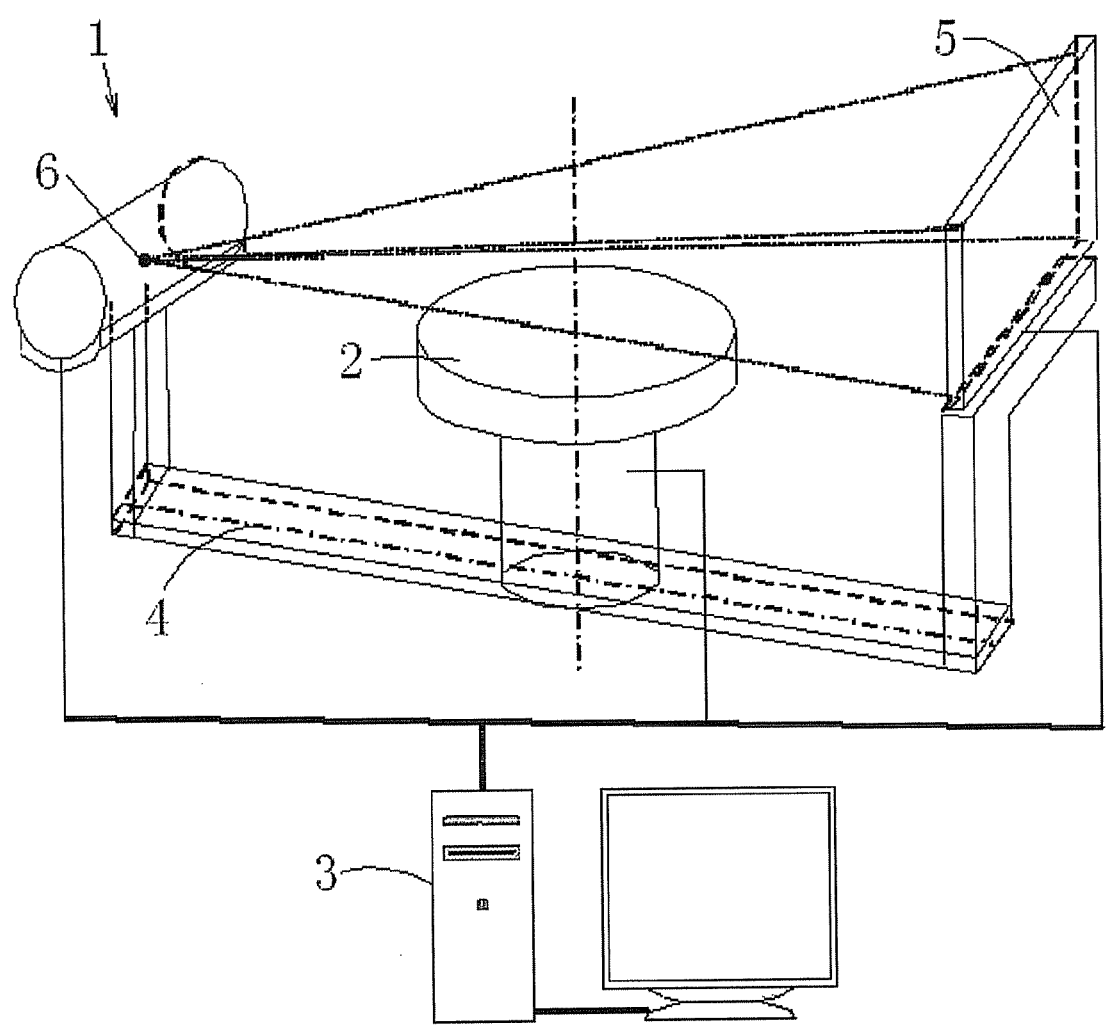
FIG. 1 is a block diagram of an X-CT scan system according to an embodiment of the invention.

1 X-ray generation device
2 object rotary support and mechanical control device thereof
3 main controlling and data processing computer
4 base
5 detector
6 X-ray source

DETAILED DESCRIPTION OF THE PREFERRED EMBODIMENTS

Reference will now be made in detail to the present embodiments of the present invention, examples of which are illustrated in the accompanying drawings, wherein like reference numerals refer to the like elements throughout. Detailed description of the known functions and structures are omitted for sake of clarity and simplicity to prevent obscuring the subject of the invention. It should be noted that the embodiments below are only for illustrating the invention, and by no ways for limiting the protection scope of the invention.

FIG. 1 is a block diagram of an X-CT scan system according to an embodiment of the invention.

As shown in FIG. 1, the X-CT scan system according to the embodiment of the invention comprises a main controlling and data processing computer 3, a base 4, a object rotary support and mechanical control device thereof 2 placed at the center of the base 4 and for placing the object to be inspected, a X-ray generation device 1 and a data acquirement system which are at two sides of the base 4. The data acquirement system comprises a planar array detector 5, a readout circuit and control logic unit for detecting X-ray projection data and the projection data on the detector. The main controlling and data processing computer 3 is responsible for the main controlling during the X-CT system operation, and processes the project data obtained by the data acquirement system to reconstruct a three-dimension image of the whole object, and display it on a display. One side of the planar array detector 5 is leveled to the prolong line of the connecting line between the X-ray source 6 of the X-ray generation device 1 and the center of the object rotary support. That is to say, the planar array detector 5 is axially deviated with one side thereof passing the axis. The X-ray source can be an X-ray tube, an accelerator radiation source or an isotope source, which depends on the object size and application circumstance. In the invention, the number of the detectors in the data acquirement system is reduced by half than that in the convention one, and the projection data related to the entire acquirement system is reduced by half.

The control, data transmission and image reconstruction of the CT system is executed by a computer workstation. The scan control information, position information and projection data are transmitted through the data acquirement system to the computer workstation, which performs the three-dimension image of the object, and displays it in three-dimension on a display. In order to precisely reconstructing the image, the X-ray imaging system should accurately measure or define the following parameters, the distance D from the X-ray source point to the detector, the distance R from the X-ray source point to the axis of the rotary support, the mapping position $P(\theta, u, v)$ on the imaging screen of the X-ray source point, the pixel size $d_x$ of the imaging screen, and the rotary degree $\theta$ of the rotary support.

According an embodiment of the invention, the reconstruction algorithm uses the cone-beam rebinning method. Firstly, the cone-beam projection data intercepted in 360 degree scope derived from the output of the detector is rebinned to parallel-beam projection data of 180 degree scan scope. A complete three-dimension image of the object is reconstructed through a convolution back-projection algorithm. The concrete implementation of the cone-beam rebinning method is as following.

(1) A virtual detector is placed at the rotary axis of the rotary support, and the intercepted cone-beam full scan projection data is rebinned to the complete parallel-beam projection data on the virtual detector in 180 degree scope according to the equations (1) and (2) below:

$$P_P(\theta, u, v) = P_F\left(\theta - \arcsin\frac{u}{R}, \frac{uD^2}{R\sqrt{D^2 - u^2}}, v\right), u \geq 0 \quad (1)$$

$$P_P(\theta, u, v) = P_F\left(\theta + \arcsin\frac{u}{R} \pm \pi, \frac{-uD^2}{R\sqrt{D^2 - u^2}}, v\right), u < 0 \quad (2)$$

In the above equations, $P_p(\theta, u, v)$ denotes a rebinned parallel-beam projection data, $\theta \in [0, \pi]$, $$u \in \left[-\frac{L}{2}, \frac{L}{2}\right]$$

denotes the lateral coordinate of rebinned parallel-beam on the virtual detector, D denotes the distance from the X-ray source point to the detector, R denotes the distance from the X-ray source point to the center of the rotary support, L denotes the width of the virtual detector of the rebinned parallel beam, $$v \in \left[-\frac{H}{2}, \frac{H}{2}\right]$$

denotes the vertical coordinate of the rebinned parallel-beam on the virtual detector, H denotes the height of the cone-beam CT detector, which is also the height of the virtual detector of the rebinned parallel-beam, $P_F$ denotes the projection data obtained by the detector of the CT system.

As can be seen from the above equations from cone-beam to parallel beam, only the projection data of $u \geq 0$ or $u < 0$ in 360 degree scope of the cone-beam CT system is required to rebin complete parallel-beam projection data in 180 degree scan scope. That is to say, what is to be obtained is only the projection data on the detector at one side of the connecting line from the X-ray source point to the center of the rotary support.

(2) The rebinned projection data is weighting-filtered depending on direction according to equation (3) below.

$$P_{FP}(\theta, u, v) = \left(\frac{R^2}{\sqrt{R^4 + R^2 v^2 - u^2 v^2}} P_P(\theta, u, v)\right) * h(u) \quad (3)$$

wherein, $P_p(\theta, u, v)$ denotes the parallel-beam projection data re-arranged in step (1), $h(u)$ denotes a filter function, which is the Ramp filter. In practices, the Ramp filter is usually replaced by R-L or S-L filter. As an example, the S-L filter function is used here, and the discrete form thereof is $$h(u) = \frac{-2}{\pi^2(4n^2 - 1)}, n = 0, \pm 1, \pm 2, \ldots \quad (4)$$

(3) The weighting-filtered parallel-beam projection data in 180 degree is backprojected according to equation (5) to obtain a complete three-dimension image of the object. The equation for the three-dimension back-projection is $$u(x, y, \theta) = y\cos\theta - x\sin\theta \quad (6)$$

$$v(x, y, z, \theta) = \frac{zR^2}{(x\cos\theta + y\sin\theta)\sqrt{\begin{array}{l}R^2 - u(x, y, \theta)^2 + \\ R^2 - u(x, y, \theta)^2\end{array}}} \quad (7)$$

Wherein (x, y, z) denotes the coordinate of the three-dimension images point of the object in a Cartesian coordinate system, and backprojection of each point corresponds to the coordinate u(x, y, θ) of the projection data point in the virtual detector, v(x, y, z, θ) is defined by the following equation:

$$f(x, y, z) = \int_0^\pi P_{FP}(\theta, u(x, y, \theta), v(x, y, z, \theta))d\theta \quad (5)$$

It should be noted that the above reconstruction equations are of a reconstruction method of X-ray cone beam scan. However, the reconstruction algorithm of X-ray fan-beam scan is the reconstruction method in a special case, in which the terms about variable v are omitted in the above equations. The detailed explanation is omitted here.

Figure 2:
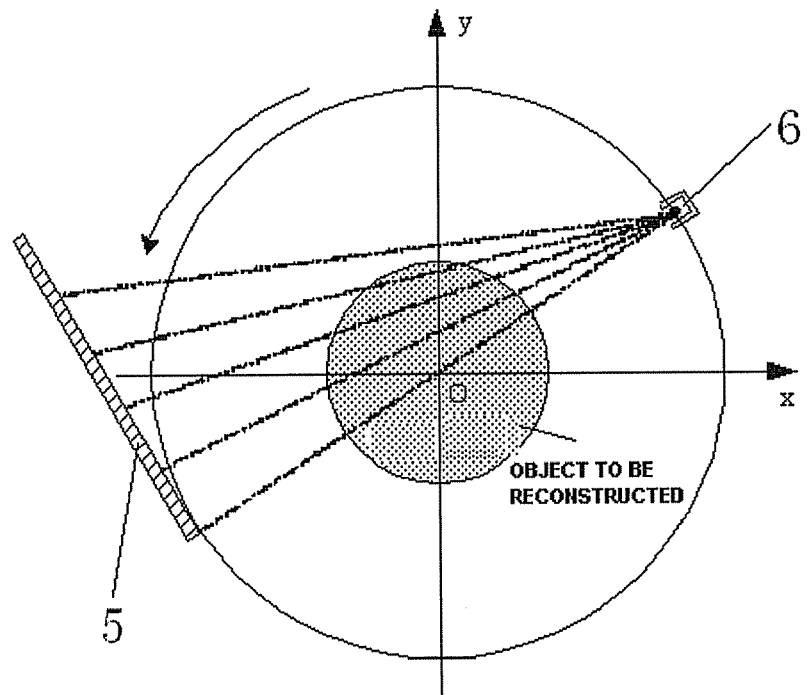
FIG. 2 is a diagram illustrating a fan-beam X-ray scan mode with the detector laterally intercepted according to an embodiment of the invention.
Figure 3:
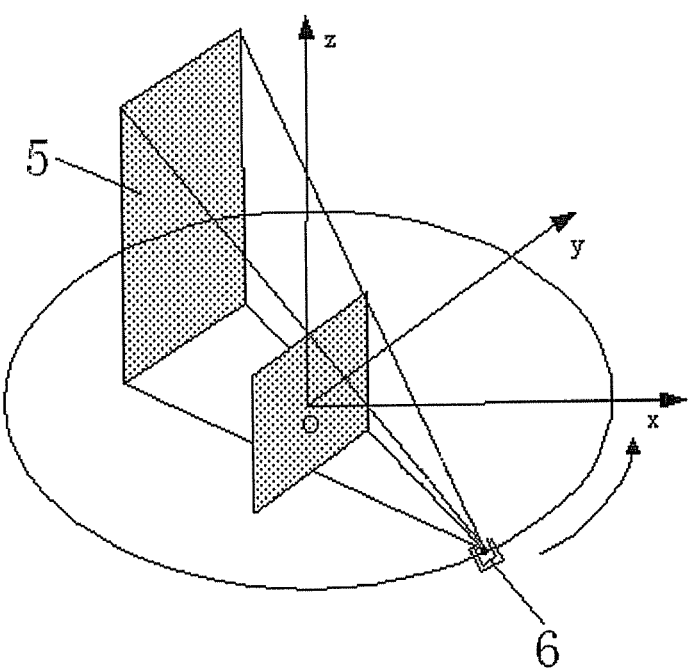
FIG. 3 is a diagram illustrating a cone-beam scan mode with the detector laterally intercepted according to an embodiment of the invention.

Referring to FIG. 2, the fan-beam X-ray only covers half of the object to be inspected. The structure is the same as that of FIGS. 1 and 3 except for the fan-beam X-ray and the detector being line array detector.

According to an embodiment of the invention, one side of the detector 5 is leveled to or beyond the prolong line of the connecting line between the X-ray source of the X-ray generation device 1 and the center of the object rotary support, the length of the beyond portion is less than the radius of the imaging field. Thus the detector in the data acquirement system is ensured to acquire data of half of the area of the object to reconstruct the image of the object. Preferably, one side of the detector 5 is leveled to the prolong line of the connecting line between the X-ray source of the X-ray generation device 1 and the center of the object rotary support, or beyond the latter by 1% of the radius of the imaging field.

FIGS. 4(a), 4(b) and 5 show part of the experiment results. FIG. 4(a) is an image reconstructed by means of fan-beam detector scan data in a Shepp-Logan head model simulation experiment. FIG. 4(b) is a section view from the middle line of the image of FIG. 4(a). FIG. 5 is a result of an experiment of the algorithm by means of the projection data of a 450 Kev CT system with a planar array detector. The experiment object is a pairline card. From the reconstruction result, it can be proved that the algorithm can reconstruct the image of the object well in the case that the detector is positioned off-center to achieve real project target.

As described above, during the X-ray cone-beam or fan-beam circular orbit scan, the detector is placed at one side of the center rotary line of the system and only covers half or little more of the object under scanning. The whole image can be reconstructed by the projection data obtained by the off-center detector scanning half of the object.

Furthermore, the mechanical structure of the X-CT scan system according to embodiments of the invention follows that of the original circular orbit scan system without special modification, what is needed is to shift the detector to cover half of the cross section of the object. In other words, compared with traditional CT scan system, the scan system according to the invention saves half of the size of the detector, and reduces the projection data amount during the scanning process of the CT system by half, and largely decreases the overhead of the hardware of the CT system, lowers the irradiation dose of the X-rays in the scanning process. The corresponding image reconstruction algorithm can use the projection data with detector laterally intercepted to accurately reconstruct all the information of the object, and obtain good reconstructed image quality.

The above description illustrates the preferable embodiments of the present invention. It can be understood by those skilled in the art that various changes, substitutions and alters to the present invention are possible without departing from the scope of the present invention. Therefore, the present invention is only limited by the following claims and the equivalents thereof.

What is claimed is:

1. An X-ray CT scan system comprising:
    a base,
    an object rotary support placed in the base which is for placing an object under inspection, the object rotary support being rotatable around a center of the object rotary support so as to rotate, but not to translate, the object in scanning a section of the object,
    an X-ray generation device and a data acquisition system comprising a detector, which are at two sides of the base respectively, characterized in that,
    one side of the detector is leveled to or slightly or beyond a prolong line of a connecting line between an X-ray source of the X-ray generation device and the center of the object rotary support, so that when viewed from the X-ray source, the detector just covers a half or a little more of the section.

2. The X-ray CT scan system according to claim 1, characterized in that the detector is a linear array detector, a curve array detector or, a planar array detector or a bend planar array detector.

3. The X ray CT scan system according to claim 1, characterized in that the X-ray generation device comprises an X-ray tube, an X-ray accelerator, or a radiation source.

* * * * *